United States Patent [19]

Yuasa et al.

[11] Patent Number: 5,463,118
[45] Date of Patent: Oct. 31, 1995

[54] N-(L-ASPARTYL)AMINO ALCOHOL DERIVATIVE AND SWEETENER CONTAINING THE SAME

[75] Inventors: Yoshifumi Yuasa; Yoshiki Okeda; Akio Tachikawa; Akira Nagakura; Haruki Tsuruta, all of Tokyo, Japan

[73] Assignee: Takasago International Corporation, Tokyo, Japan

[21] Appl. No.: 254,442

[22] Filed: Jun. 2, 1994

Related U.S. Application Data

[63] Continuation of Ser. No. 578, Jan. 4, 1993, abandoned, which is a continuation of Ser. No. 784,074, Oct. 30, 1991, abandoned, which is a continuation of Ser. No. 453,216, Dec. 21, 1989, abandoned, which is a continuation of Ser. No. 250,585, Sep. 29, 1988, abandoned.

[30] Foreign Application Priority Data

| Sep. 29, 1987 | [JP] | Japan | 62-242573 |
| Apr. 21, 1988 | [JP] | Japan | 63-96859 |
| Jun. 28, 1988 | [JP] | Japan | 63-158034 |

[51] Int. Cl.$^6$ .......................... C07C 61/12; A23L 1/236
[52] U.S. Cl. .............................. 562/502; 426/548
[58] Field of Search .................... 562/502; 426/548

[56] References Cited

U.S. PATENT DOCUMENTS

| 3,907,766 | 9/1975 | Fujino | 260/112.5 |
| 4,654,439 | 3/1987 | Roy | 562/503 |

FOREIGN PATENT DOCUMENTS

| 203540 | 12/1986 | European Pat. Off. . |
| 255343 | 2/1988 | European Pat. Off. . |

*Primary Examiner*—Michael L. Shippen
*Attorney, Agent, or Firm*—Sughrue, Mion, Zinn, Macpeak & Seas

[57] ABSTRACT

(2R,3R)-3-N-(L-aspartyl)amino-1-(1-methyl-2-norbornyl)-2-butanol and (2R,3R)-3-N-(L-aspartyl)amino-1-(3-methyl-2-norbornyl)-2-butanol as well as a sweetener comprising the same are disclosed. These compounds, which have excellent sweetness characteristics and are stable in acidic aqueous solutions, are highly useful as a sweetener in various fields.

2 Claims, 1 Drawing Sheet

N-(L-ASPARTYL)AMINO ALCOHOL DERIVATIVE AND SWEETENER CONTAINING THE SAME

This is a Continuation of Application No. of prior parent application Ser. No. 08/000,578 filed on Jan. 4, 1993 (now abandoned) which is a continuation of prior application Ser. No. 07/784,074 filed on Oct. 30, 1991 (now abandoned), which is a continuation of prior parent application Ser. No. 07/453,216 filed Dec. 21, 1989 (now abandoned), which in turn is a continuation of prior parent application Ser. No. 07/250,585 filed Sep. 29, 1988 (now abandoned).

FIELD OF THE INVENTION

The present invention relates to (2R,3R)-3-N-(L-aspartyl)amino- 1-(1-methyl-2-norbornyl)-2-butanol or (2R,3R)-3-N-(L-aspartyl)amino-1-(3-methyl-2-norbonyl)-2-butanol, each of which has excellent sweetness characteristics and is widely useful in, for example, foods and drugs as a sweetener highly stable in aqueous solutions, as well as a sweetener containing the same.

BACKGROUND OF THE INVENTION

In addition to sucrose which is being most widely employed as a good sweetener, there have been used various sweeteners including sugars such as fructose, isomerized sugars and glucose, sugar alcohols such as sorbitol and mannitol, natural sweetening substances such as glycyrrhizin, stevioside and thaumatin, and artificial sweetening substances such as saccharin sodium, sodium cyclamate, acesulfame-K (3,4-dihydro- 6-methyl-1,2,3-oxathiazin-4-one 2,2-dioxide potassium salt), and aspartame.

Recently there have been an increasing number of patients suffering from dental caries as well as obesity, diabetes, cardiopathy, hypertension, renal diseases, etc., which are mainly caused by excessive calorie intake. Thus, it has been required to develop low-calorie sweeteners for the treatment of these diseases or for the maintenance of good health. As the result of attempts for satisfying the above requirement, some products have come into the market. However, artificial sweeteners are strictly regulated because of the toxicity thereof. On the other hand, natural sweeteners are unsatisfactory in sweetness characteristics and aftertaste. In addition, the latter are expensive.

Recently the use of L-aspartyl-L-phenylalanine methyl ester, which will be referred to as aspartame or "APM" hereinafter, has been permitted. This compound is becoming a major artificial sweetener.

There have been reported more than 500 dipeptides including APM (cf. Ariyoshi, *Kagaku Sosetsu*, No. 14, 85 to 128 (1976); Iwamura, *J. Med. Chem.*, 24, 572 to 583 (1981); and A. Van der Heijden et al., *Chemical Senses and Flavor*, 4(2), 141 to 152 (1979)). However there are few substances having a degree of sweetness 500 times or more as high as that of sucrose. Further these dipeptides, which are esters, would be hydrolyzed in aqueous solutions or undergo a dealcoholation reaction with an amino group of an aspartate residue to thereby form a diketopiperazine derivative, which would frequently eliminate or alter the sweetness characteristics of the same.

Among dipeptide esters known so far, L-aspartyl-DL-aminomalonic acid methyl fenchyl diester reported by Fujino et al. (cf. JP-B-52-34622, JP-A-49-30566, and *Chem. Pharm. Bull.*, 24(9), 2112 (1976)) has the highest degree of sweetness, though it is inferior to APM in stability at 80° C. and at a pH of 4. (The terms "JP-A" and "JP-B" mean an "unexamined published Japanese patent application" and an "examined Japanese patent publication", respectively.) Recently JP-A-62-30748 has reported that L-aminocarboxylic acid amides of alkyl-substituted cycloalkyls or bicycloalkyl-substituted amino alcohols or aminoketones are 30 to 600 times sweeter than sucrose. Further JP-A-56-127339 has reported branched amides of L-aspartyl-D-amino acid, and U.S. Pat. No. 4,423,029 has reported (S)-3-amino-4-4-oxobutyric acid compounds. However the degrees of sweetness of these compounds are only 200 to 300 times as high as that of sucrose and thus they are not completely satisfactory.

SUMMARY OF THE INVENTION

It is an object of the present invention to provide a sweetening compound which has sweetness characteristics similar to those of sucrose, a high degree of sweetness and yet low calories and is highly stable in acidic aqueous solutions as well as a sweetener containing the same.

BRIEF DESCRIPTION OF THE ACCOMPANIYING DRAWING

FIG. 1 is a FIGURE showing the stability of aqueous solutions of the compounds of the present invention at a pH of 4 at 80° C., wherein A shows (2R,3R)-3-N-(L-aspartyl)amino- 1-2butanol, B shows (2R,3R)-3-N-(L-aspartyl)amino-1- 2-butanol, and C shows 3-N-(L-aspartyl)amino-1-d-α-fenchyl-2-butanol, while APM represents aspartame and AMF represents L-aspartyl-DL-aminomalonic acid methylfenchyl ester.

DETAILED DESCRIPTION OF THE INVENTION

Figure 1:
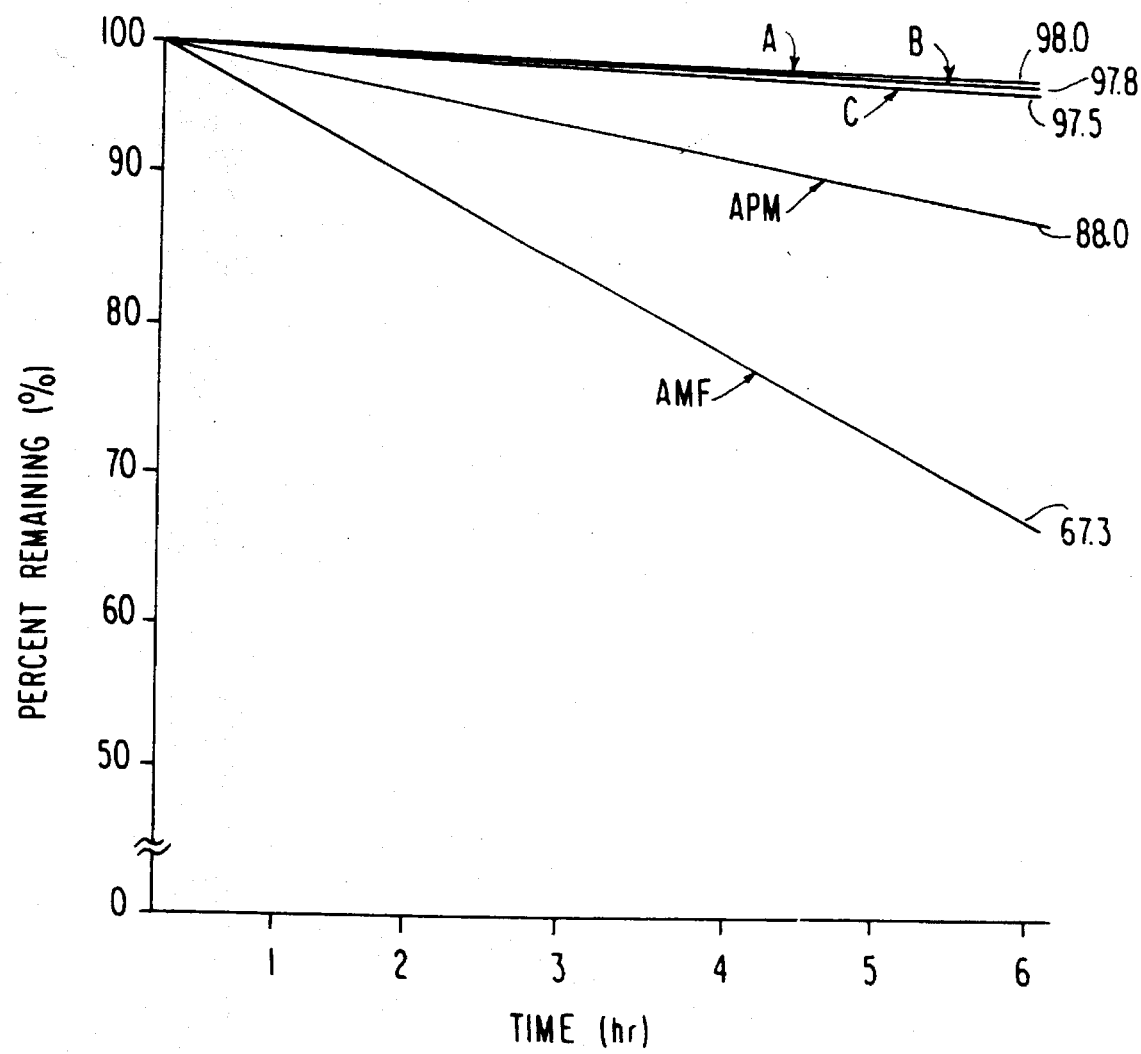

The present inventors have previously found that an ester of L-aspartyl-D-alanine, in particular with fenchyl alcohol, generally shows a high degree of sweetness. In order to improve both of the degree of sweetness and stability of this compound, it has been attempted to convert the ester portion into other functional groups such as a hydroxyl group and to synthesize and evaluate an L-aspartylfenchylamino alcohol derivative by condensing an amino alcohol derivative having a fenchyl group with L-aspartic acid. As a result, it has been found that this L-aspartylfenchylamino alcohol derivative not only has a high degree of sweetness and excellent sweetness characteristics but also is excellent in solubility in water and stability in acidic aqueous solutions. Thus the inventors have applied for a patent on this compound (cf. JP-A-63-39846).

Subsequent studies by the inventors have disclosed that the sweetness essentially depends on the absolute configuration at the (a) and (b) positions in the following formula (i). For example, compounds of the following general formula:

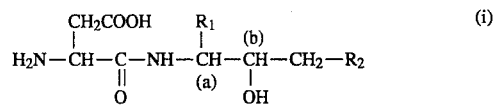

wherein $R_1$ is methyl group while $R_2$ is fenchyl group: had degrees of sweetness as shown below (RS shows a racemate):

| (a) | (b) | Degree of sweetness |
|---|---|---|
| RS | RS | 1,800 |
| S | R | 0 |
| S | S | 0 |
| R | S | 0 |
| R | R | 12,500 |

Thus the compound of the absolute configuration at the (a) and (b) positions of (R,R) shows the highest degree of sweetness followed by the one of (RS,RS). In contrast thereto, those of (S,S), (S,R) and (R,S) each show scarcely any sweetness. The absolute configurations at the (a) and (b) positions are determined by resolving amino alcohol derivatives with tartaric acid to thereby give p-bromobenzoic acid amide derivatives of the following formula (ii) and then analyzing the crystal structures thereof with X-rays:

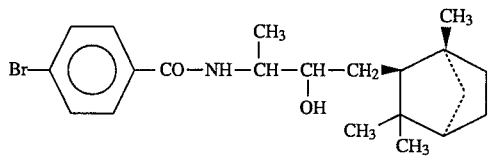

wherein ... is located below the paper plane while ▬ is located above the same.

The inventors have further examined the correlation between the structures, in particular, the $R_2$ site in the formula (i), of these compounds and the sweetness characteristics of the same and consequently obtained some findings. Namely, the sweetness characteristics of norbornane skeleton compounds are evaluated by regarding those immediately exhibiting a sweet taste and less aftertaste, similar to the sweetness characteristics of sucrose, as preferable. Thus, the following compounds are highly evaluated in this order.

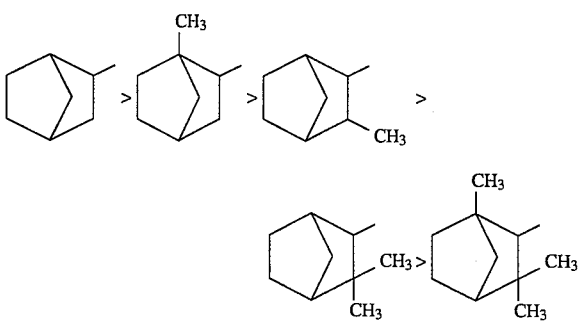

Based on these findings, the inventors have further examined the relationship among the sweetness characteristics, in particular, the degree and qualities of sweetness and the chemical and steric structures thereof. As a result, it has been found that (2R,3R)-3-N-(L-aspartyl)amino- 1-(1-methyl-2-norbornyl)-2-butanol and (2R,3R)-3-N-(L-aspartyl)amino-1-(3-methyl-2-norbornyl)- 2-butanol have excellent sweetness characteristics, thus completing the present invention.

Accordingly the present invention provides (2R, 3R)-3-N-(L-aspartyl)amino-1-(1-methyl-2-norbornyl)-2-butanol and (2R,3R)-3-N-(L-aspartyl)amino-1-(3-methyl-2-norbornyl)- 2-butanol and a sweetener containing the same.

There are the following optical isomers of a 1- or 3-methyl-2-norbornyl skeleton.

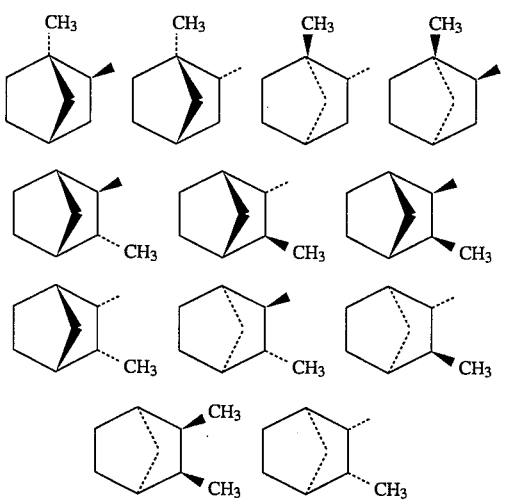

The (2R,3R)-3-N-(L-aspartyl)amino-1-(1-methyl-2-norbornyl)- 2-butanol or (2R,3R)-3-N-(L-aspartyl)amino-1-(3-methyl-2-norbornyl)-2-butanol derived from each of these 1- or 3-methyl-2-norbornyl optical isomers may be obtained by appropriately selecting the starting material.

For example, (2R,3R)-3-N-(L-aspartyl)amino-1- 2-butanol and (2R,3R)-3-N-(L-aspartyl)amino-1-2butanol, each falling within the scope of the present invention, may be synthesized by the following schemes (A) and (B) respectively wherein Ts represents p-toluenesulfonyl group, Cbz represents carbobenzoxy group, and Bz represents benzyl group.

Reaction scheme (A):

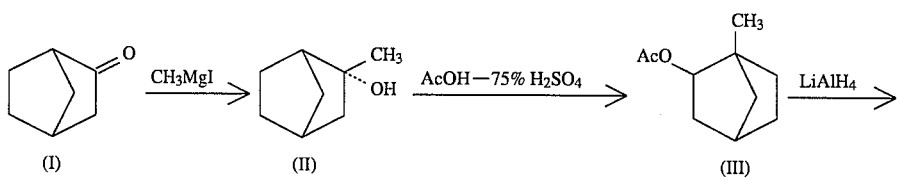

-continued
Reaction scheme (A):

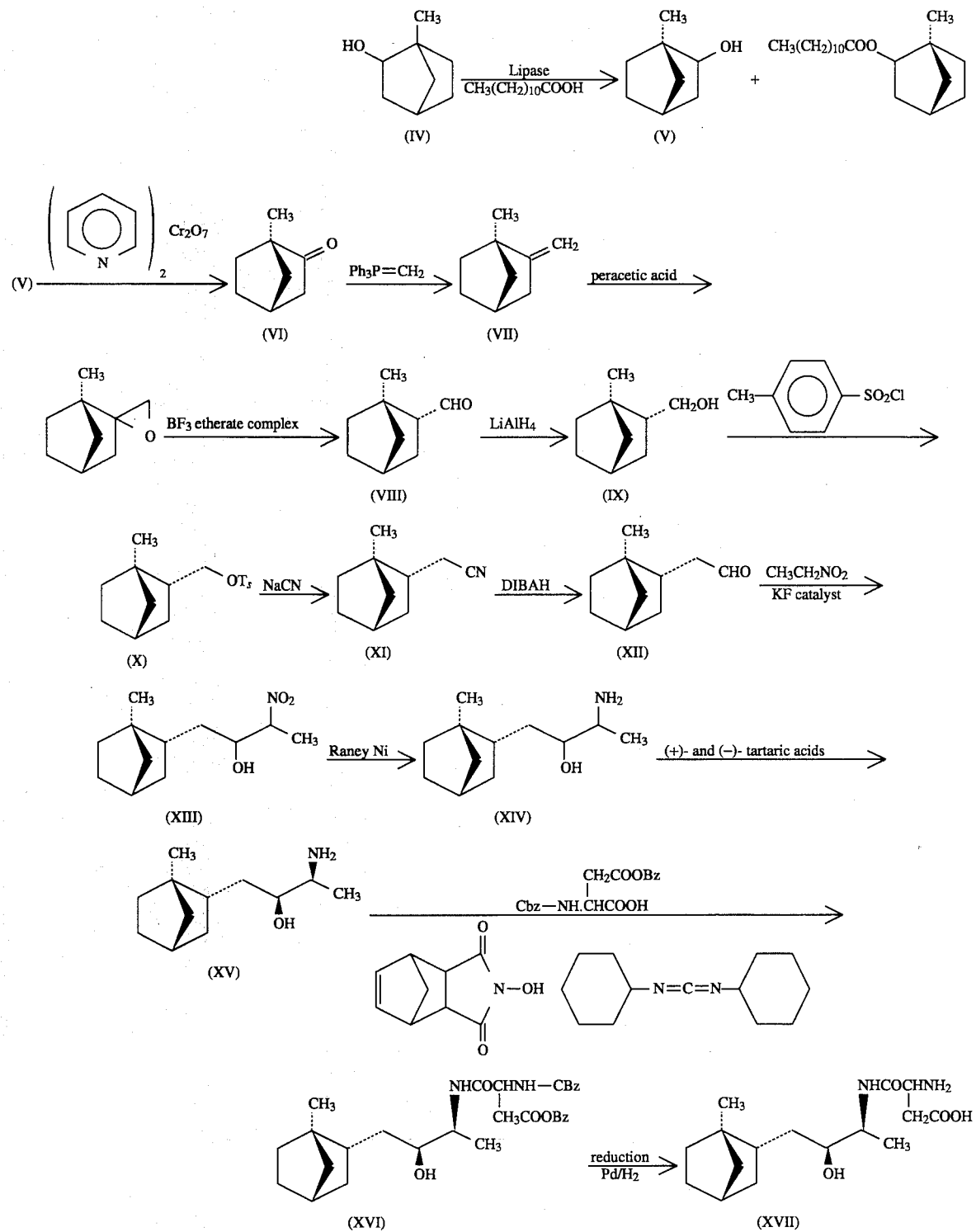

As shown in the above reaction sheme (A), (2R,3R)-3-N-(L-aspartyl)amino-1- 2-butanol can be obtained in the following manner.

Norbornanone (I) is reacted with methylmagnesium iodide to give 2-methyl-2-norbornanol (II). The compound (II) is reacted with acetic acid and a 75% solution of sulfuric acid to give 2-acetoxy-1-methylnorbornane (III) which is then converted into 1-methyl- 2-norbornanol (IV) with lithium-aluminum hydride. Then the compound (IV) is enzymatically resolved according to the method reported by Christian Triantaphylides et al., *Tetrahedron Letters*, 26(15), 1857 (1985) to give (1S)-1-methyl-2-norbornanol (V). This optically active alcohol (V) is then oxidized with pyridine dichromate complex to give (1S)-1-methyl-2-norbornanone (VI). The compound (VI) is reacted with methyltriphenylphosphonium bromide in the presence of n-butyllithium to give (1S)-2-methylenenorbornane (VII) which is then treated with peracetic acid to give an epoxy compound. This epoxy compound is treated with a boron trifluoride etherate complex to give (1S,2S)-1-methyl- 2-norbornyl aldehyde (VIII) which is then reduced with lithium aluminum hydride to give (1S,2S)-1-methyl- 2-hydroxymethylnorbornane (IX).

Then this alcohol compound (IX) is treated with p-toluenesulfonyl chloride to give a tosylate (X). This tosylate (X) is reacted with sodium cyanide to give (1S,2S)-1-methyl-2-cyanolmethylnorbornane (XI). This compound (XI) is reduced with diisobutylaluminum hydride (DIBAH) to give (1S, 2S)-1-methylnorbornane-2-acetaldehyde (XII). This compound (XII) is subjected to aldol condensation with nitroethane in the presence of potassium fluoride to give 1-3-nitro-2-butanol (XIII). This compound (XIII) is then reduced with Raney nickel to give diastereomers of 1-3-amino- 2-butanol (XIV). These diastereomers are resolved with (+)- and (−)- tartaric acids to give a (2R,3R)-compound (XV).

The 1-(2R,3R)-3-amino- 2-butanol (XV) thus obtained is reacted with an active ester, which is obtained by condensing monobenzyl carbobenzoxy-L-aspartate with N-hydroxy-5-norbornene- 2,3-dicarboxyimide and cyclohexylcarbodiimide, to give (2R,3R)-3-N-(carbobenzoxy-L-aspartyl-β-benzyl-ester)amino-1-2-butanol (XVI). The protective group of the compound (XVI) is hydrogenotically eliminated with palladium/carbon. Thus (2R,3R)-3-N-(L-aspartyl)amino-1-2-butanol (XVII), i.e., one of the compounds of the present invention is obtained.

Reaction Scheme (B):

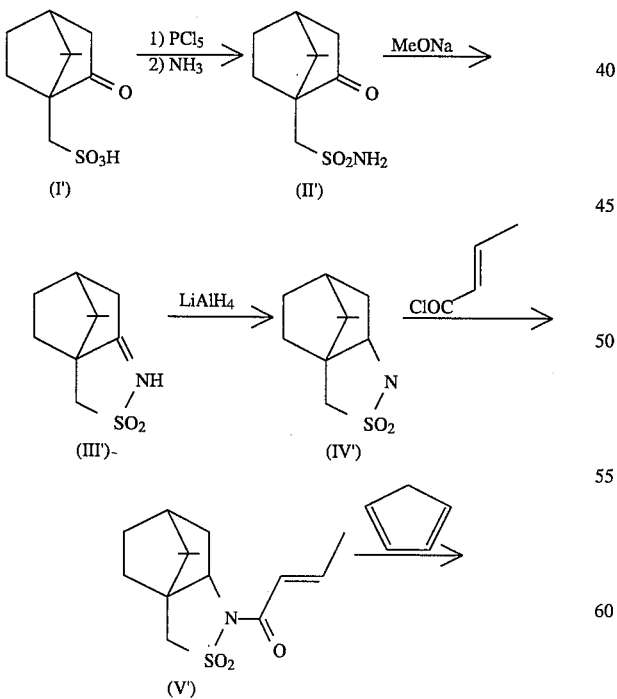

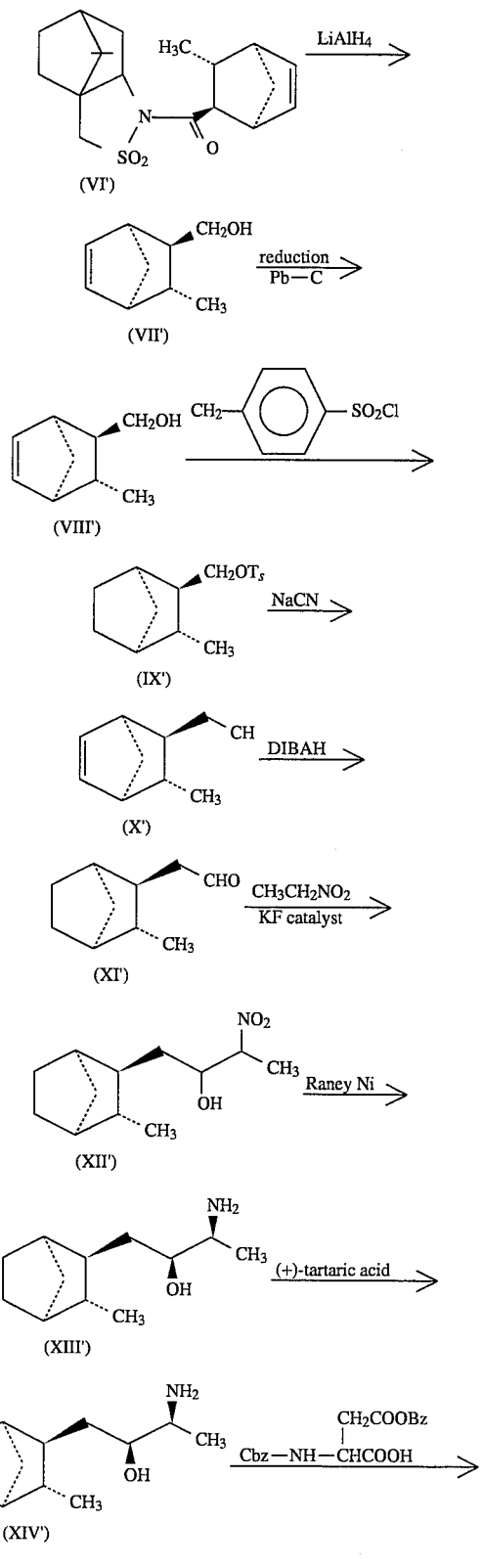

-continued
Reaction Scheme (B):

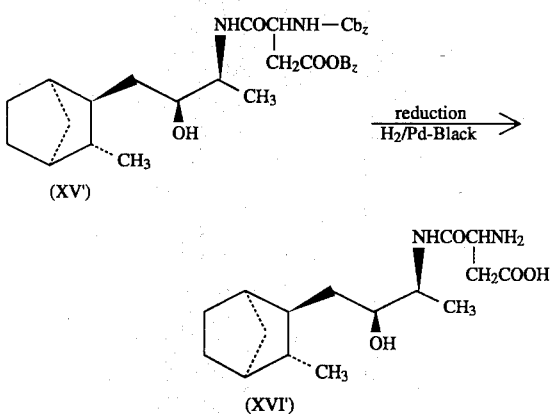

On the other hand, (2R,3R)-3-N-(L-aspartyl)-amino- 1-2-butanol can be obtained by the reaction scheme (B) as shown above.

Namely, a readily available starting material (+)-camphor-10-sulfonic acid (I') (manufactured. by Aldrich Chemical Co., Inc.) is treated according to the method reported by Wolfgang Oppalzer et al., *Helvetica Chemica Acta*, 67, 1397 (1984) and *Tetrahedron*, 42, 4035 (1986). The starting material is first reacted with phosphorus pentachloride and ammonia to give (+)-camphor- 10 -sulfonamide (II'). This compound (II') is then reacted with sodium methylate to give an intramolecular imine (III') whose unsaturated bond is then reduced with lithium aluminum hydride to give a sultam (IV'). The sultam (IV') is reacted with crotonyl chloride to give an acylated compound (V'). This compound (V') is subjected to Diels-Alder reaction with cyclopentadiene to give an adduct (VI') whose camphane ring moiety is then eliminated with lithium aluminum hydride to give (5S,6R)-6-methyl-5-hydroxymethyl-2-norbornene (VII'). This compound (VII') is then catalytically reduced with palladium/carbon to give (2S,3R)-2-hydroxymethyl-3-methylnorbornane (VIII'). This compound (VIII') is treated in the same manner as described in the reaction scheme (A) regarding the (1S,2S)-2-hydroxymethyl-1-methyl-norbornane (IX) to give (2R,3R)-3-N-(L-aspartyl)amino-1- 2-butanol (XVI') which is another compound of the present invention.

The compounds of the present invention, i.e., (2R,3R)-3-N-(L-aspartyl)amino-1-(1-methyl-2-norbornyl)- 2-butanol and (2R,3R)-3-N-(L-aspartyl)amino-1-(3-methyl- 2-norbornyl)-2-butanol are colorless and odorless powders and highly soluble in water. A diluted aqueous solution thereof has sweetness characteristics closely similar to those of sucrose and gives almost no disagreeable tastes such as bitter taste, bad taste and unpleasant aftertaste. Table 1 shows the results of the evaluation of the sweetness characteristics thereof. In particular, the features of the compounds of the present invention reside in that they are excellent in stability in acidic aqueous solutions and good in heat stability.

The compounds of the present invention can be widely used in various foods, beverages, toothpastes, cigarettes and cosmetics to which sweeteners are generally added, regardless of the products shape. For example, they may be used for soft drinks such as fruit juice, fruit drinks and soda pop, lactic acid beverages and carbonated beverages which are optionally powdered, alcoholic beverages such as rice wine (sake), synthetic rice wine, fruit liquors and sweetened rice wine for seasoning (mirin), cold sweets such as ice cream and sherbet, fruits in syrup, seasonings such as miso paste, soy sauce, sauce, vinegar, dressing, mayonnaise and ketchup, cakes such as rice cakes, bread, cakes, biscuits and crackers, chocolate, chewing gum, jelly, sweet jelly of beans, jam, marmalade, modified powdered milk, various seaweeds or shellfishes boiled in sweetened soy sauce, canned foods, delicacies of domestic animal meat, meat products such as bacon, ham and sausage, fishmeat products such as boiled fish paste on a board (kamaboko) and that on a rod (chikuwa), compound seasonings, lipsticks and drugs for oral administration.

The compounds of the present invention can be used either in the form of a powder as they stand or in the form of a solution in an appropriate solvent. The amount of the same to be added may be appropriately selected depending on, for example, the type of the compound, the purpose, the subject, the addition means and the type and amount of other sweetener(s) and seasoning(s), if any, to be used together.

To further illustrate the present invention, the following Examples, Referential Examples and Use Examples will be given.

EXAMPLE 1

1—1) Synthesis of 2-methyl-2-norbornanol (II)

A Grignard reagent was prepared from 96 g (4.0 M) of magnesium flakes and 553.0 g (3.9M) of methyl iodide in 600 ml of absolute diethyl ether under a nitrogen gas stream in the conventional manner. 225.0 g (2.05M) of norbornanone (I) (manufactured by Aldrich Chemical Co., Inc.) was added dropwise thereto at room temperature and the resulting mixture was stirred at room temperature over night. The reaction mixture was poured into 800 ml of a saturated aqueous solution of ammonium chloride. The organic phase was collected and dried over anhydrous magnesium sulfate. After evaporation of the ether, the residue was distilled under reduced pressure to give 250.1 g (theoretical yield: 97%) of the aimed compound (II) as a colorless oily material. b.p.: 75° C./18 mmHg.

1–2) Synthesis of 1-methyl-2-norbornyl acetate (III)

1 ml of 75% sulfuric acid was added to 240.0 g (1.9M) of the alcohol (II) obtained in 1—1) above and 500 ml of glacial acetic acid and the resulting mixture was stirred at 60° C. for three hours. After cooling, the reaction mixture was diluted with 3 1 of water and then neutralized with sodium carbonate.

Subsequently it was extracted-thrice with 300 ml portions of diethyl ether and dried over anhydrous magnesium sulfate. After evaporation of the ether, the residue was distilled under reduced pressure to give 297.2 g (theoretical yield: 93%) of the aimed compound (III) as a colorless oily material. b.p.: 82° to 83° C./17 mmHg.

1-3) Synthesis of 1-methyl-2-norbornanol (IV)

290.0 g (1.73M) of the acetate (III) obtained in 1–2) above dissolved in 300 ml of absolute diethyl ether was added to 65.2 g (1.7M) of lithium aluminum hydride suspended in 800 ml of absolute diethyl ether at room temperature under a nitrogen gas stream. Then the resulting mixture was heated under reflux for six hours and stirred at room temperature over night. Subsequently 500 ml of a 5% aqueous solution of sulfuric acid was slowly added to the reaction mixture with stirring under ice-cooling. The ether phase was collected and dried over anhydrous magnesium sulfate. After evaporation of the ether, the residue was distilled under reduced pressure to give 209 g (theoretical yield: 96%) of the aimed compound (IV) as a colorless oily material. b.p.: 83° C./20 mmHg.

1-4) Synthesis of (1S)-1-methyl-2-norbornanol (V)

209 g (1.66M) of the alcohol (IV) obtained in 1-3) above and 332 g (1.66M) of lauric acid were dissolved in 660 ml of n-hexane and 66 g of Lipase MY (manufactured by Meito Sangyo K.K.) was added thereto. The resulting mixture was reacted at 35° to 40° C. under stirring for three days. After filtering off the enzyme and evaporating the n-hexane, the residue was distilled under reduced pressure to give 79.6 g (theoretical yield: 76%) of the aimed optically active alcohol (V). b.p.: 82° C./19 mmHg.

1-5) Synthesis of (1S)-1-methyl-2-norbornanone (VI)

79.6 g (0.63M) of the optically active alcohol (V) obtained in 1-4) above was dissolved in 300 ml of methylene chloride and the resulting solution was added dropwise to a suspension of 304 g (0.81M) of pyridine dichromate in 700 ml of methylene chloride at room temperature. Then the resulting mixture was stirred for three days. The obtained reaction mixture was diluted with 1 l of diethyl ether and filtered through celite. The filtrate was dried over anhydrous magnesium sulfate and the solvent was evaporated. The residue was distilled under reduced pressure to give 50.4 g (theoretical yield: 64.5%) of the aimed compound (VI) as a colorless oily material. b.p.: 70° C./20 mmHg.

$[\alpha]_D^{20} = +32.0°$ (c=3.09, CHCl$_3$)

1-6) Synthesis of (1S)-2-methylenenorbornane (VII)

143 g (0.4M) of methyltriphenyl phosphonium bromide was added to a mixed solution of 260 ml of a 15% solution of n-butyllithium in hexane and 500 ml of diethyl ether at room temperature under anhydrous conditions over 30 minutes. Then the mixture was stirred at room temperature for four hours and 50.0 g (0.4M) of the ketone (VI) obtained in 1-5) above was added dropwise thereto. The resulting mixture was heated under stirring over night. The reaction mixture was cooled to room temperature and the triphenylphosphine oxide thus formed was filtered. 350 ml of water was added to the filtrate, and the organic phase was collected and dried over anhydrous magnesium sulfate. After evaporation of the solvent, the residue was distilled under reduced pressure to give 31.8 g (theoretical yield: 65%) of the aimed compound (VII) as a colorless oily material. b.p.: 135° to 137° C.

1-7) Synthesis of (1S,2S)-1-methyl-2-norbornyl aldehyde (VIII)

70 g of 40% peracetic acid was added to 31.0 g (0.25M) of the alkene (VII) obtained in 1-6) above, 48.6 g (0.46M) of sodium carbonate and 100 ml of methylene chloride at 10° C. The resulting mixture was stirred at room temperature over night and then poured into 500 ml of water. The organic phase was washed twice with a saturated aqueous solution of Mohr's salt and subsequently with water and then dried over anhydrous magnesium sulfate. After evaporation of the solvent, 38.6 g of a yellow oily material was obtained. 450 ml of benzene and 13 ml of a boron trifluoride etherate complex were added thereto and the resulting mixture was vigorously stirred for one minute. 450 ml of water was added to the reaction mixture, and the organic phase was collected, washed with water and dried over anhydrous magnesium sulfate. After evaporation of the solvent, the residue was distilled under reduced pressure to give 20.1 g (theoretical yield: 58%) of the aimed compound (VIII) as a colorless oily material. b.p.: 75° C./15 mmHg.

1-8) Synthesis of (1S,2S)-1-methyl-2-hydroxymethylnorbornane (IX)

20.1 g (0.15M) of the aldehyde (VIII) obtained in 1-7) above was dissolved in 20 ml of absolute diethyl ether and the obtained solution was added dropwise to a suspension of 1.9 g (50 mM) of lithium aluminum hydride in 100 ml of absolute diethyl ether under a nitrogen gas stream at room temperature. The resulting mixture was heated under reflux for six hours and then ice-cooled. 100 ml of 5% sulfuric acid was slowly added dropwise thereto. The ether phase was collected and dried over anhydrous magnesium sulfate. After evaporation of the ether, the residue was distilled under reduced pressure to give 19.6 g (theoretical yield: 96%) of the aimed compound (IX) as a colorless oily material. b.p.: 65° to 68° C./1 mmHg.

1-9) Synthesis of (1S,2S)-1-methyl-2-cyanomethylnorbornane (XI)

19.0 g (0.14M) of the alcohol (IX) obtained in 1-8) above and 54.3 g (0.28M) of p-toluenesulfonyl chloride were dissolved in 200 ml of dry pyridine under a nitrogen gas stream and the resulting mixture was stirred at 10° C. for eight hours. The reaction mixture was poured into water and extracted with 150 ml of benzene. The extract was washed with 1N hydrochloric acid and then with water and dried over anhydrous magnesium sulfate. After evaporation of the solvent, 39.9 g (theoretical yield: 100%) of a tosylate (X) was obtained as a colorless oily material.

Then 39.9 g (0.14M) of the tosylate (X) and 7.6 g (0.16M) of sodium cyanide were dissolved in 850 ml of dimethyl sulfoxide and reacted at 90° C. for five hours. The reaction mixture was poured into 400 ml of a saturated aqueous solution of ammonium chloride and extracted twice with 150 ml portions of methylene chloride. The organic phase was washed with water seven times and dried over anhydrous magnesium sulfate. After evaporation of the solvent, 19.5 g (theoretical yield: 98%) of the aimed nitrile derivative (XI) was obtained as a colorless oily material.

1-10) Synthesis of (1S,2S)-1-methylnorbornane-2-acetaldehyde (XII)

19.5 g (0.13M) of the nitrile (XI) obtained in 1-9) above was dissolved in 200 ml of absolute ether under a nitrogen gas stream and 160 ml of a 1M solution of diisobutylaluminum hydride in hexane was added dropwise thereto at room temperature. Then the resulting mixture was stirred for one hour, poured into ice/water and acidified with 1N hydrochloric acid. The organic phase was collected and dried over anhydrous magnesium sulfate. After evaporation of the solvent, the residue was distilled under reduced pressure to give 19.0 g (theoretical yield: 96%) of the aimed compound (XII) as a colorless oily material. b.p.: 45° to 47° C./0.5 mmHg.

1-11) Synthesis of 1-3-nitro- 2-butanol (XIII)

38.0 g (0.25M) of the acetaldehyde derivative (XII) obtained in 1-10) above was dissolved in 60 ml of isopropyl alcohol under a nitrogen gas stream and 1.62 g (28 mM) of potassium fluoride and 26.7 g (0.35M) of nitroethane were added thereto. The resulting mixture was stirred at room temperature overnight. The reaction mixture was poured into 350 ml of diethyl ether, and the organic phase was collected, washed with water and then with 0.5N hydrochloric acid and dried over anhydrous magnesium sulfate. After evaporation of the solvent, 55.9 g (theoretical yield: 97%) of the aimed compound (XIII) was obtained as a colorless oily material.

1-12) Synthesis of 1-3-amino- 2-butanol (XIV)

10 g (44 mM) of the nitro alcohol derivative (XIII)

obtained in 1–11) above was dissolved in 400 ml of ethanol and 8 g of a suspension of Raney nickel in ethanol was added thereto. The resulting mixture was sealed into a 1 l autoclave under a hydrogen gas pressure of 25 kg/cm² and reacted therein at room temperature for eight hours. After completion of the reaction, the catalyst was filtered off and the filtrate was concentrated under reduced pressure. The residue was distilled under reduced pressure to thereby give 7.2 g (theoretical yield: 83%) of the aimed compound (XIV) as a colorless oily material. b.p.: 108° to 111° C./1 mmHg.

1–13) Synthesis of 1-( 2R,3R)-3-amino-2-butanol (XV)

45.0 g (0.23M) of the amino alcohol derivative (XIV) obtained in 1-12) above was added to a solution of 34.1 g (0.23M) of (+)-tartaric acid dissolved in 200 ml of ethanol and the resulting mixture was reacted at 50° C. for one hour. The solvent was distilled off under reduced pressure to give 79.1 g of crude crystals (m.p.: 160° to 162° C.). These crystals were recrystallized from hot ethanol four times to give 9.9 g of purified crystals. These crystals were thoroughly made alkaline with an aqueous solution of potassium carbonate and then extracted twice with 50 ml portions of methylene chloride. The extract was dried over anhydrous magnesium sulfate and the solvent was evaporated. Thus 5.89 g (15.7 mM) of a colorless oily material was obtained. To the product thus obtained, a solution of 2.36 g (15.7 mM) of (–)-tartaric acid dissolved in 50 ml of ethanol was added and the mixture was reacted at 50° C. for one hour. The reaction mixture was concentrated under reduced pressure and the crude crystals thus formed were repeatedly recrystallized from hot ethanol four times. The purified crystals thus obtained were thoroughly made alkaline with an aqueous solution of potassium carbonate and treated in the same manner as that described above. Thus 0.15 g (0.17 mM) of the titled compound (XV) was obtained as a colorless oily material. The characteristic values of this compound are as follows:

$[\alpha]_D^{20} = +0.42°$ (c=0.5, methanol)
NMR (CDCl$_3$, δ):
1.08(3H, s, ring CH$_3$ group),

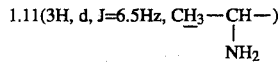
1.11(3H, d, J=6.5Hz, C$\underline{H}_3$—CH—)
          |
         NH$_2$

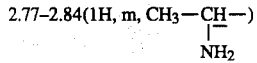
2.77–2.84(1H, m, CH$_3$—C$\underline{H}$—)
              |
             NH$_2$

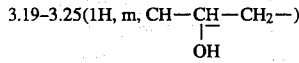
3.19–3.25(1H, m, CH—C$\underline{H}$—CH$_2$—)
              |
             OH 1–14) Synthesis of (2R,3R)-3-N-(carbobenzoxy-L-aspartyl-β-benzyl ester)amino-1-2-butanol (XVI)

0.27 g (0.76 mM) of N-carbobenzoxy-L-aspartic acid-β-benzyl ester (manufactured by Kokusan Kagaku K.K.) was dissolved in 10 ml of dioxane and 0.14 g (0.76 mM) of N-hydroxy-5-norbornene-2,3-dioxyimide (manufactured by Peptide Kenkyusho K.K. ) was added thereto. To the obtained mixture, 0.17 g (0.83 mM) of dicyclohexyl carbodiimide was added under ice-cooling with stirring. The resulting mixture was stirred at room temperature for four hours. The dicyclohexyl urea thus formed was filtered off and 0.15 g (0.76 mM) of the amino alcohol (XV) obtained in 1-13) above dissolved in 3 ml of dioxane was added to the filtrate under cooling and stirring. Subsequently the reaction mixture was stirred at room temperature over night to complete the reaction. After evaporation of the solvent, the residue was dissolved in 30 ml of ethyl acetate, washed successively with 10% citric acid, a 4% aqueous solution of sodium bicarbonate and a saturated solution of sodium chloride and then dried over anhydrous magnesium sulfate. After evaporation of the solvent, the residue was purified by silica gel column chromatography to give 0.22 g (theoretical yield: 86%) of the titled compound (XVI) as a colorless oily material.

1–15 ) Synthesis of (2R,3R)-3-N-(L-aspartyl)amino-1-2-butanol (XVII)

0.22 g (0.41 mM) of the (2R,3R)-3-N-(carbobenzoxy-L-aspartyl-β-benzyl ester)amino-1- 2-butanol (XVI) obtained in 1-14) above was dissolved in 10 ml of methanol and catalytically reduced in the presence of palladium black at room temperature for four hours. After completion of the reaction, the catalyst was filtered off and the methanol was distilled off under reduced pressure. To the residue, an appropriate amount of n-hexane was added to give 0.12 g (theoretical yield: 94%) of the titled compound (XVII) as crystals. The characteristic values of this compound are as follows:

m.p.: 147–150° C.
$[\alpha]_D^{20} = +0.68°$ (c=0.5, methanol)
Ms: 294(M$^+$ –18), 235, 161, 141, 125, 70 and 40 (base)
NMR (CD$_3$OD, δ):
1.08(3H, s, ring CH$_3$ group),

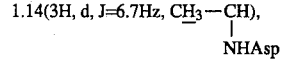
1.14(3H, d, J=6.7Hz, C$\underline{H}_3$—CH),
                |
               NHAsp

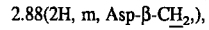
2.88(2H, m, Asp-β-C$\underline{H}_2$,),

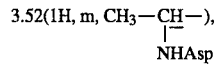
3.52(1H, m, CH$_3$—C$\underline{H}$—),
              |
             NHAsp

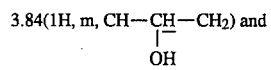
3.84(1H, m, CH—C$\underline{H}$—CH$_2$) and
              |
             OH The term "ASP" means aspartyl group.

EXAMPLE 2

2–1) Synthesis of (2S,3R)-2-hydroxymethyl-3-methyl-norbornane (VIII')

40.5 g (0.29M) of (5S,6R)-6-methyl-5-hydroxymethyl-2-norbornene (VII') prepared from (+)-camphor- 10-sulfonic acid (I') (manufactured by Aldrich Chemical Co., Inc.) was dissolved in 250 ml of methanol and catalytically reduced in the conventional manner, i.e., by stirring the same in the presence of palladium black at room temperature for ten hours. After completion of the reaction, the catalyst was filtered off and the methanol was distilled off under reduced pressure. The residue was distilled under reduced pressure to give 39.5 g (theoretical yield: 95%) of the aimed compound (VIII') as a colorless oily material. b.p.: 97° to 99° C./16 mmHg.

2—2) Synthesis of (2S,3R)-2-cyanomethyl-3-methyl-norbornane (X')

39.5 g (0.28M) of the norbornane derivative (VIII') obtained in 2-1) above and 113 g (0.59M) of p-toluene-sulfonyl chloride were dissolved in 400 ml of dry pyridine under a nitrogen gas stream and the resulting solution was stirred at 10° C. for eight hours. After completion of the reaction, the reaction mixture was poured into water, extracted with 300 ml of benzene, washed with 1N hydrochloric acid and then with water and dried over anhydrous magnesium sulfate. After evaporation of the solvent, 82.3 g (theoretical yield: 100%) of a tosylate (IX') was obtained as a colorless oily material. Then 82.3 g (0.28M) of this tosylate (IX') and 15.7 g (0.32M) of sodium cyanide were dissolved in 750 ml of dimethyl sulfoxide under a nitrogen gas stream and reacted at 90° C. for five hours. The reaction mixture was poured into 800 ml of a saturated aqueous solution of ammonium chloride and extracted twice with 300 ml portions of methylene chloride. The organic phase was washed with water seven times and dried over anhydrous magnesium sulfate. After evaporation of the solvent, 40.2 g (theoretical yield: 96%) of the aimed nitrile derivative (X') was obtained as a colorless oily material.

2–3) Synthesis of (2S,3R)-3-methylnorbornane-2-acetaldehyde (XI')

40.2 g (0.27M) of the nitrile derivative (X') obtained in 2—2) above was dissolved in 500 ml of absolute diethyl ether under a nitrogen gas stream and 330 ml of a 1M solution of diisobutylaluminum hydride in hexane was added dropwise thereto at room temperature. After completion of the addition, the resulting mixture was stirred for one hour, then poured into ice/water and acidified with 1N hydrochloric acid. The ether phase was collected and dried over anhydrous magnesium sulfate. After evaporation of the ether, the residue was distilled under reduced pressure to give 30.4 g (theoretical yield: 83%) of the aimed acetaldehyde derivative (XI'). b.p.: 90° to 92° C./15 mmHg.

2–4) Synthesis of 1-3-nitro- 2-butanol (XII')

34.4 g (0.23M) of the acetaldehyde derivative (XI') obtained in 2-3) above was dissolved in 50 ml of isopropyl alcohol under a nitrogen gas stream. 1.47 g (25 mM) of potassium fluoride and 24.2 g (0.32M) of nitroethane were added thereto and the resulting mixture was stirred at room temperature over night. The reaction mixture was poured into 300 ml of diethyl ether and extracted with diethyl ether. The organic phase was collected, washed with water and then with 0.5N hydrochloric acid and dried over anhydrous magnesium sulfate. After evaporation of the ether, 50.6 g (theoretical yield: 97%) of the aimed nitro alcohol derivative (XII') was obtained as a colorless oily material.

2–5) Synthesis of 1-3-amino- 2-butanol (XIII')

10 g (44 mM) of the nitro alcohol derivative (XII') obtained in 2-4) above was dissolved in 400 ml of ethanol and 8 g of a Raney nickel suspension in ethanol was added thereto. The mixture was sealed within a 1 l autoclave under a hydrogen gas pressure of 25 kg/cm$^2$ and reacted therein at room temperature for eight hours. After completion of the reaction, the catalyst was filtered off and the filtrate was concentrated under reduced pressure. The residue was distilled to give 7.0 g (theoretical yield: 81%) of the aimed amino alcohol derivative (XIII') as a colorless oily material. b.p.: 103° C./1 mmHg.

2–6) Resolution of (2R,3R)-1- 3-amino-2-butanol (XIV')

33.0 g (0.17M) of the amino alcohol derivative (XIII') obtained in 2-5) above was added to a solution prepared by dissolving 25.2 g (0.17M) of (+)-tartaric acid in 150 ml of ethanol and reacted therewith at 50° C. for one hour. The solvent was distilled off under reduced pressure to give 58.2 g of crude crystals (m.p.: 154° to 156° C.). These crystals were repeatedly recrystallized from hot ethanol six times to give 3.16 g of purified crystals. These crystals were thoroughly made alkaline with an aqueous solution of potassium carbonate and extracted twice with 50 ml portions of methylene chloride. The extract was dried over anhydrous magnesium sulfate. After evaporation of the solvent, 1.64 g (8.3 mM) of the titled compound (XIV') was obtained as a colorless oily material. The characteristic values of this compound are as follows:

$[\alpha]_D^{20} = +19.3°$ (c=1, ethanol)
NMR (CDCl$_3$, δ):
0.95(3H, s, ring C$\underline{H}_3$ group), 1.10(2H, d, J=6.6Hz, C$\underline{H}_3$—CH—)
       |
       NH$_2$ 2.71–2.78(1H, m, CH$_3$—C$\underline{H}$—) and
           |
           NH$_2$ 3.71–3.22(1H, m, CH—C$\underline{H}$—CH$_2$—)
            |
            OH 2–7) Synthesis of (2R,3R)-3-N-(carbobenzoxy-L-aspartyl-β-benzyl ester)amino-1-2-butanol (XV')

2.97 g (8.3 mM) of carbobenzoxy-L-aspartic acid-β-benzyl ester (manufactured by Kokusan Kagaku K.K.) was dissolved in 70 ml of dioxane and 1.50 g (8.3 mM) of N-hydroxy- 5-norbornene-2,3-dicarboxyimide (manufactured by Peptide Kenkyusho K.K.) was added thereto. The resulting mixture was stirred under ice-cooling and 1.90 g (9.1 mM) of dicyclohexylcarbodiimide was further added thereto. The resulting mixture was stirred for four hours at room temperature. The dicyclohexyl urea thus formed was filtered off and 1.64 g (8.3 mM) of the amino alcohol derivative (XIV') obtained in 2-6) above dissolved in 10 ml of dioxane was added thereto under ice-cooling and stirring. The reaction mixture was stirred at room temperature over night to complete the reaction. After evaporation of the solvent, the residue was dissolved in 200 ml of ethyl acetate and washed successively with a 10% aqueous solution of citric acid, a 4% aqueous solution of sodium bicarbonate and a saturated aqueous solution of sodium chloride. Then it was dried over anhydrous magnesium sulfate. After evaporation of the solvent, the residue was purified by silica gel column chromatography to give 2.33 g (theoretical yield: 83%) of the titled compound (XV') as a colorless oily material.

2–8) Synthesis of (2R,3R)-3-N-(L-aspartyl)amino-1-2-butanol (XVI')

2.31 g (4.3 mM) of the (2R,3R)-3-N-(carbobenzoxy-L-aspartyl-β-benzyl ester)amino-1- 2-butanol (XV') obtained in 2-7) above was dissolved in 40 ml of methanol and catalytically reduced in the presence of palladium black at room temperature for four hours. After completion of the reaction, the catalyst was filtered off and the methanol was distilled off under reduced pressure. To the residue, an appropriate amount of n-hexane was added to give 1.21 g (theoretical yield: 90%) of the titled compound (XVI') as crystals. The characteristic values of this compound are as follows:

m.p.: 127–133° C.
$[\alpha]_D^{20} = +23.8°$ (c=1.0, methanol)
Ms: 294(M$^+$–18), 235, 162, 142, 125, 88, 70 and 44 (base)
NMR (CD$_3$OD, δ):
0.95(3H, s, ring CH$_3$ group), 1.16(3H, d, J=6.9Hz, C$\underline{H}_3$—CH—),
          |
          NH.Asp -continued 2.86(2H, m, Asp-β-C$\underline{H_2}$), 3.53(1H, m, CH$_3$—C$\underline{H}$—),
    |
    NH.Asp 3.93(1H, m, C$\underline{H}$—CH$_2$—), and
    |
    OH 4.16(1H, m, Asp-α-C$\underline{H}$).

EXAMPLE 3

Each of (2R,3R)-3-N-(L-aspartyl)amino-1-2-butanol (XVI') obtained in Example 2, 2–8), which will be referred to as "compound A" hereinafter, the (2R,3R)-3-N-(L-aspartyl)amino- 1-2-butanol (XVII) obtained in Example 1, 1–15), which will be referred to as "compound B" hereinafter, APM and sucrose was dissolved in water. The threshold value of each compound was determined by a limit method by a panel consisting of five skilled flavorists. Table 1 shows the results.

TABLE 1

| Sweetener | Taste intesity threshold value (%) | Degree of sweetness (time) |
|---|---|---|
| Compound A | 0.00024 | 2,500 |
| Compound B | 0.00018 | 3,300 |
| APM | 0.004 | 150 |
| Sucrose | 0.6 | 1 |

EXAMPLE 4

Each of compounds A and B, APM and L-aspartyl-DL-aminomalonic acid methyl fenchyl ester as disclosed in JP-A-49-30566, which will be abbreviated as "AMF" hereinafter, was dissolved in a 0.1M phosphate buffer solution (pH 4.0) at a concentration of 0.2%. The obtained solution was maintained at 80° C. and the percent remaining was monitored by high performance liquid chromatography with a lapse of time to thereby compare the stabilities of these solutions with each other. FIG. 1 shows the results. FIG. 1 obviously indicates that the compounds of the present invention are superior to the control compounds in stability.

EXAMPLE 5

Compounds of absolute configurations (a) and (b) of (RS,RS) and (S,S) were prepared by way of trial, and the degrees and characteristics of sweetness thereof were evaluated.

The sweetness characteristics were evaluated in the following manner.

A standard beverage was prepared by adding the following materials to 1600 ml of carbonated water:

| | |
|---|---|
| Glucose | 200 g |
| Citric acid | 1.5 g |
| Cola essence | 2 ml |
| Water | 400 ml |

Various sweeteners were added to the standard beverage each at a definite concentration. The beverages thus obtained were stored at 37° C. for 26 days and then evaluated by nine panelists according to the following criterion. Table 2 shows the results.

Evaluation:

1—Extremely poor.

2—Very poor.

3—Poor.

4—Somewhat poor.

5—Good.

6—Very good.

7—Excellent.

8—Very excellent.

9—Extremely excellent.

TABLE 2

| Compound | Absolute configuration (a) | Absolute configuration (b) | M.P. (°C.) | Degree of sweetness based on sucrose (time) | Concentration (ppm) | Average score |
|---|---|---|---|---|---|---|
| 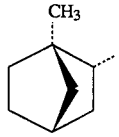 | R | R | 147–150 | 3,300 | 30 | 6.3 |
| 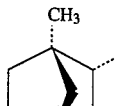 | RS | RS | 143–146 | 800 | 165 | 5.1 |
| 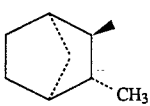 | R | R | 127–133 | 2,500 | 35 | 6.2 |
| 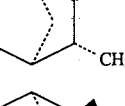 | RS | RS | 133–139 | 850 | 160 | 5.0 |
| 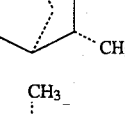 | S | S | 150–154 | 0 | 0 | — |
| 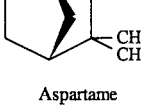 | RS | RS | 129–136 | 1,800 | 110 | 4.1 |
| Aspartame | — | — | — | 250 | 520 | 5.8 |

These results obviously indicate that the (S,S)-compound showed scarcely any sweetness while the (RS,RS)-compound was inferior to the (R,R)-compound not only in degree of sweetness but also in sweetness characteristics. From the commercial viewpoint, a sweetener compound should have an appropriate degree of sweetness and excellent sweetness characteristics. Thus the compounds of the present invention satisfy these requirements.

REFERENTIAL EXAMPLE 1—1

Resolution of (2S,3S)-1- 3-amino-2-butanol 58.2 g of the crude crystals obtained during the course of the procedure of Example 2, 2–6 ) were recrystallized twice from 95% hot ethanol. The mother liquor thus obtained was concentrated to give 5.1 g of crystals. These crystals were repeatedly recrystallized from 95% hot ethanol three times. Thus 0.85 g of a tartarate (m.p.: 200°–201° C.) was obtained as purified crystals.

Then these crystals were thoroughly made alkaline with an aqueous solution of potassium carbonate and extracted twice with 50 ml portions of methylene chloride. The extract was dried over anhydrous magnesium sulfate. After evaporation of the solvent off, 0.44 g (2.2 mM) of an oily material was obtained. The characteristic values of this compound are as follows:

NMR (CDCl$_3$, δ):
0.92(3H, s, ring CH$_3$ group),

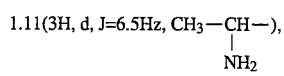

2.68–2.75(1H, m, CH$_3$—CH—) and

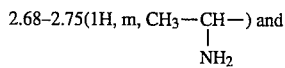

3.11–3.16(1H, m, CH$_3$—CH—CH).

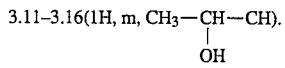

REFERENTIAL EXAMPLE 1–2

Synthesis of (2S, 3S)-3-N-(L-aspartyl)amino- 1-2-butanol

The (2S,3S)-1-3-amino- 2-butanol obtained in Referential Example 1—was treated in the same manner as in Example 2, 2–7) to give (2S,3S)-3-N-(carbobenzoxy-L-aspartyl-β-benzyl ester)-amino- 1-2-butanol which was then treated in the same manner as in Example 2, 2–8) to give the titled compound. This compound showed scarcely any sweetness. The characteristic values thereof are as follows:

m.p.: 150–154° C.
[α]$_D^{20}$ = −30.0° (c=1, methanol)
Ms: 295, 235, 159, 143, 125, 70 and 44 (base)
NMR (CD$_3$OD, δ):
0.92(3H, s, ring C$\underline{H}_3$ group), 1.19(3H, d, J=6.9Hz, C$\underline{H}_3$—CH—),
  |
  NH.Asp 2.95(2H, m, Asp-β-C$\underline{H}_2$), 3.48(1H, m, CH$_3$—C$\underline{H}$—),
  |
  NH.Asp 3.95(1H, m, C$\underline{H}$—CH$_2$—) and
  |
  OH 4.22(1H, m, Asp-α-C$\underline{H}$).

REFERENTIAL EXAMPLE 2

Synthesis of 3-N-(L-aspartyl)-amino- 1-d-α-fenchyl-2-butanol 214 g (1.4M) of d-fenchone was reacted with 500 g of methyltriphenylphosphonium bromide to give 1,3,3-trimethyl- 2-methylenebicyclo heptane. This product was reacted with a synthetic gas to give fenchyl acetaldehyde (b.p.: 75° C./1 mmHg) which was then subjected to aldol condensation with nitroethane. The resulting product was hydrogenated in the presence of a Raney nickel catalyst to give 1-d-α-fenchyl-3-amino-2-butanol (b.p.: 103° C./1 mmHg). This product was treated in the same manner as in Example 2, 2–7) to give 3-N-(carbobenzoxy-L-aspartyl-β-benzyl ester)amino-1-d-α-fenchyl- 2-butanol which was then treated in the same manner as in Example 2, 2–8) to give the titled compound (m.p.: 129°–136° C.) which will be referred to as "compound C" hereinafter.

For the sake of convenience for use, 1 g of each of compounds A and B was thoroughly mixed with 99 g of glucose to give a powder sample of a concentration of 1%. Each amount described in the following Use Examples will be expressed in terms of this 1% sample.

Use Example 1: Cold sweet

Water was added to the following materials to give the total amount of 1000 g:

| | |
|---|---|
| Powdered starch syrup | 180 g |
| Thickener | 3 g |
| Citric acid | 2 g |
| Common salt | 0.1 g |
| Strawberry essence | 1 ml |
| Compound A | 8 g. |

The stock solution thus obtained was frozen to give a strawberry cold sweet which gave a refreshing sweetness and was tasty.

Use Example 2: fruit juice-free carbonated beverage

Water was added to the following materials to give the total amount of 400 ml:

| | |
|---|---|
| Glucose | 200 g |
| Citric acid | 1.5 g |
| Lemon essence | 2 ml |
| Compound B | 4.6 g. |

1600 ml of carbonated water was added thereto to give a carbonated beverage which showed excellent sweetness characteristics similar to those of sucrose.

Use Example 3: Toothpaste

Water was added to the following materials to give the total amount of 1000 g:

| | |
|---|---|
| Calcium hydrogenphosphate | 500 g |
| Carboxymethyl cellulose | 11 g |
| Sodium laurylsulfate | 15 g |
| Glycerol | 250 g |
| Compound A | 0.4 g |
| Toothpaste flavor | 9.5 g |
| Sodium benzoate | 0.5 g. |

This composition was kneaded in a blender to give a toothpaste which showed refreshing sweetness without any bitterness and gave preferable results.

Use Example 4: Sherbet

Water was added to the following materials to give the total amount of 1000 g:

| | |
|---|---|
| Powdered starch syrup | 210 g |
| Stabilizer | 3 g |
| Citric acid | 1 g |
| Compound B | 5.5 g |
| Yellow color No. 5 | q.p. |
| Orange flavor | 1 g. |

The obtained composition was prepared into a sherbet by a freezer. The product was comparable to the ordinary one containing refined sugar in taste.

The present invention provides 3-N-(L-aspartyl)-amino alcohol derivatives having stereospecificity as well as a sweetener containing the same. These compounds have sweetness characteristics similar to those of sucrose and high degrees of sweetness and are stable in acidic aqueous solutions. Thus they are highly useful as a sweetener in various fields without any restriction.

While the invention has been described in detail and with reference to specific embodiments thereof, it will be apparent to one skilled in the art that various changes and modifications can be made therein without departing from the spirit and scope thereof.

What is claimed is:

1. A single isomer (2R,3R)-3-N-(L-aspartyl)amino-1-2-butanol.

2. A sweetener comprising a single isomer (2R,3R)-3-N-(L-aspartyl)amino-1-2-butanol and food acceptable additives or solvents.

* * * * *